US012632934B2

(12) United States Patent
Conti et al.

(10) Patent No.: US 12,632,934 B2
(45) Date of Patent: May 19, 2026

(54) METHOD OF REMOVING ARTIFACTS IN AN ECOGRAPHIC DOPPLER VIDEO

(71) Applicant: SYNDIAG S.R.L., Turin (IT)

(72) Inventors: Daniele Conti, Turin (IT); Rosilari Bellacosa Marotti, Turin (IT); Flavia De Simone, Turin (IT)

(73) Assignee: SYNDIAG S.R.L., Turin (IT)

( * ) Notice: Subject to any disclaimer, the term of this patent is extended or adjusted under 35 U.S.C. 154(b) by 255 days.

(21) Appl. No.: 18/257,623

(22) PCT Filed: Dec. 15, 2021

(86) PCT No.: PCT/IB2021/061798
§ 371 (c)(1),
(2) Date: Jun. 15, 2023

(87) PCT Pub. No.: WO2022/130257
PCT Pub. Date: Jun. 23, 2022

(65) Prior Publication Data
US 2024/0112309 A1 Apr. 4, 2024

(30) Foreign Application Priority Data

Dec. 15, 2020 (WO) .................. PCT/IB2020/061992
Feb. 19, 2021 (IT) ......................... 102021000003929

(51) Int. Cl.
*G06T 5/70* (2024.01)
*A61B 8/00* (2006.01)
(Continued)

(52) U.S. Cl.
CPC ............... *G06T 5/70* (2024.01); *A61B 8/488* (2013.01); *A61B 8/5269* (2013.01);
(Continued)

(58) Field of Classification Search
CPC .. G06T 5/70; G06T 5/30; G06T 7/248; G06T 7/74; G06T 7/90; G06T 2207/10016;
(Continued)

(56) References Cited

U.S. PATENT DOCUMENTS 5,899,864 A 5/1999 Arenson et al.
6,511,426 B1 1/2003 Hossack et al.
(Continued)

OTHER PUBLICATIONS

Tzu-Hao Yu, et al., Reconfigurable Color Doppler DSP Engine for High-Frequency Ultrasonic Imaging Systems, SiPS, 2007, pp. 187-192.

*Primary Examiner* — Chineyere Wills-Burns
*Assistant Examiner* — Phuong Hau Cai
(74) *Attorney, Agent, or Firm* — Bayramoglu Law Offices LLC

(57) ABSTRACT

A denoising method for removing artefacts acquiring a plurality of frames composing an ultrasound video; identifying pixels containing doppler activation. The method further includes generating for each frame, a first set of image data to associate to each pixel position of the corresponding frame at least a first or a second category to categorize the pixels of the corresponding frame and identifying for each frame the pixels containing doppler activation, generating at least a persistence sequence associated to a frame portion containing identification data ordered according to the frame sequence such that adjacent identification data in the sequence refers to consecutive frames, and in the persistence sequence, calculating the length of each persistence sub-sequence comprising consecutive identification data having the first value. In addition, automatically calculating a reference threshold is automatically calculated and the doppler pixels are eliminated if the latter belong to a persistence sequence below the threshold.

20 Claims, 8 Drawing Sheets

(51) Int. Cl.

| | |
|---|---|
| *G01S 7/52* | (2006.01) |
| *G06T 5/30* | (2006.01) |
| *G06T 7/246* | (2017.01) |
| *G06T 7/73* | (2017.01) |
| *G06T 7/90* | (2017.01) |
| *G06V 10/56* | (2022.01) |
| *G06V 10/75* | (2022.01) |
| *G06V 10/762* | (2022.01) |
| *G06V 10/764* | (2022.01) |
| *G06V 20/70* | (2022.01) |
| *G16H 30/40* | (2018.01) |

(52) U.S. Cl.
CPC ............ *G01S 7/52077* (2013.01); *G06T 5/30* (2013.01); *G06T 7/248* (2017.01); *G06T 7/74* (2017.01); *G06T 7/90* (2017.01); *G06V 10/56* (2022.01); *G06V 10/751* (2022.01); *G06V 10/762* (2022.01); *G06V 10/764* (2022.01); *G06V 20/70* (2022.01); *G16H 30/40* (2018.01); *G06T 2207/10016* (2013.01); *G06T 2207/10024* (2013.01); *G06T 2207/10132* (2013.01); *G06T 2207/20036* (2013.01); *G06T 2207/20084* (2013.01); *G06T 2207/30101* (2013.01)

(58) Field of Classification Search
CPC . G06T 2207/10024; G06T 2207/10132; G06T 2207/20036; G06T 2207/20084; G06T 2207/30101; G06T 2207/20024; G06T 2207/20112; G06T 2207/30004; G06T 5/50; A61B 8/488; A61B 8/5269; A61B 8/06; G01S 7/52077; G01S 15/8979; G06V 10/56; G06V 10/751; G06V 10/762; G06V 10/764; G06V 20/70; G16H 30/40

See application file for complete search history.

(56) References Cited

U.S. PATENT DOCUMENTS

| | | | |
|---|---|---|---|
| 2012/0101384 A1 | 4/2012 | Migita et al. | |
| 2019/0261952 A1 | 8/2019 | Freiburger et al. | |
| 2020/0184614 A1* | 6/2020 | Zhang | ...................... G06T 5/50 |
| 2021/0055398 A1* | 2/2021 | Loupas | ............... A61B 8/5246 |

* cited by examiner

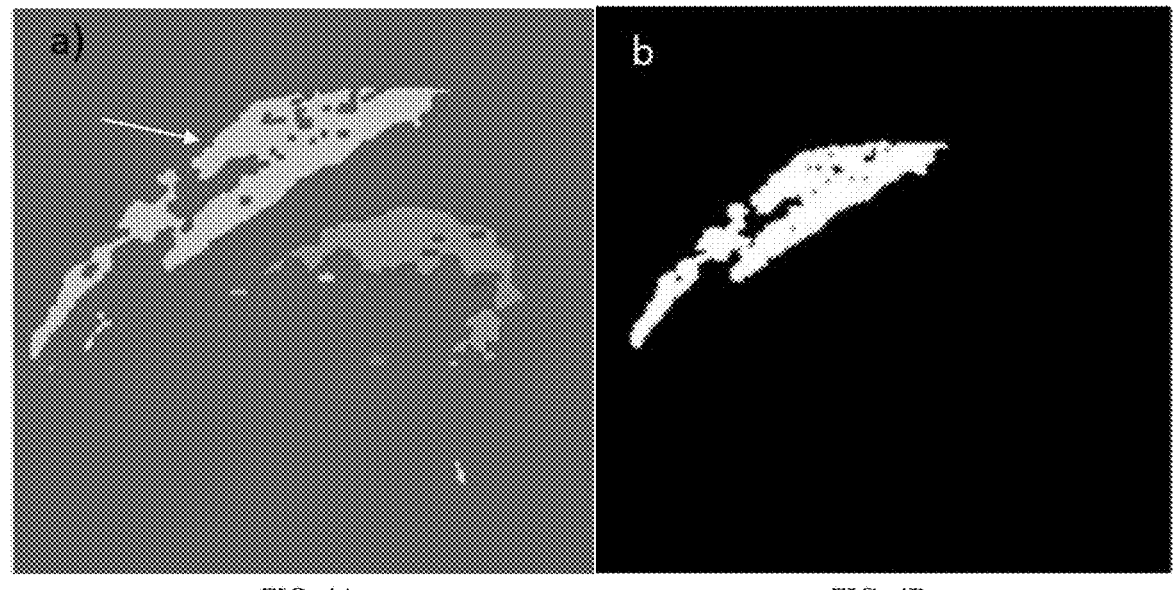
FIG. 4A                    FIG. 4B
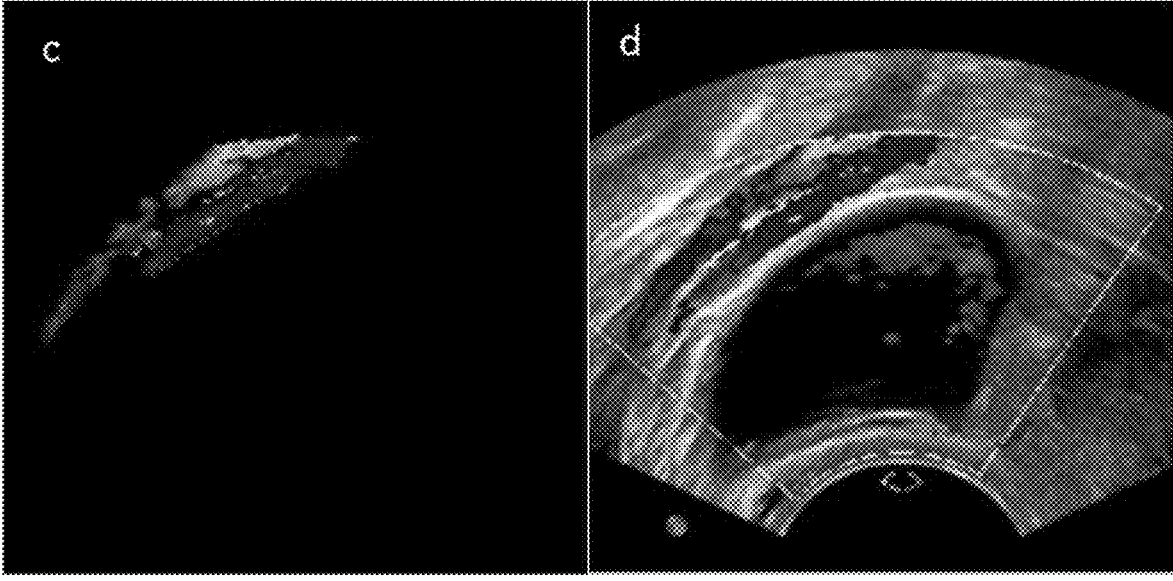
FIG. 4C                    FIG. 4D

METHOD OF REMOVING ARTIFACTS IN AN ECOGRAPHIC DOPPLER VIDEO

CROSS REFERENCE TO THE RELATED APPLICATIONS

This application is the national phase entry of International Application No. PCT/IB2021/061798, filed on Dec. 15, 2021, which is based upon and claims priority to Italian Patent Application No. 102021000003929 filed on Feb. 19, 2021 and International Application No. PCT/IB2020/061992 filed on Dec. 15, 2020, and the entire contents of which are incorporated herein by reference.

TECHNICAL FIELD

The present invention relates to a method of removing artifacts contained in an ecographic doppler video.

BACKGROUND

Ultrasound imaging techniques are commonly used to produce diagnostic images of the internal features of an object, such as human anatomy.

Ultrasound imaging is a technique that reproduces on a two-dimensional image an anatomical section of the human body corresponding to the scan plane. The mechanism by which the information contained in echo signals is transformed into a two-dimensional image is complex and consists of several steps. Some of these depend on the propagation of ultrasound in biological tissues, others are dependent on the equipment technology or how the operator handles them. Ultrasounds are generated by the transducer, and properly focused, they propagate in the tissues with an approximately constant speed with slight variations from tissue to tissue depending on density or acoustic impedance. The contact between ultrasound and various anatomical structures marks the beginning of various physical phenomena such as reflection, dispersion, diffraction and absorption. This first two of the above phenomena generate the echo signal that returns to the transducer and, properly processed, creates the ultrasound image. Basically, the information contained in the raw signal is not sufficient to create an ultrasound image, but it must be integrated with other essential information: the first one is the depth of the signal origin, which is established as a function of the time elapsed between a beam emission and a echo signal return; the second one is the signal direction along the lines composing the scan plane. In other words, to generate an ultrasound image it is necessary that these three information are acquired for each point of the scanning area.

Ultrasound imaging devices are sophisticated instruments capable of handling several imaging modalities. A simplified block diagram of an ultrasound imaging device comprises:
- a pulse generator responsible for creating electrical signals;
- a piezoelectric transducer driven to perform both duties as source and receiver. As a source, the transducer is responsible for sending ultrasonic acoustic signals generated by converting electrical pulses into a wave. The acoustic wave pulse travelling through the tissue is partially reflected by materials with different acoustic impedance. Therefore, as a receiver, the transducer is responsible for detecting the reflected pulses and converting them into radio frequency (RF) electrical signals;

- a TGC module that acts on received signal by amplifying it in a proportional way to the depth of the echo signal generation and to the signal return time compensating therefore the gain in order to correctly represent the acoustic impedance difference of the surfaces constituting the discontinuities. In other words, signals reaching the probe from deeper planes of the sound field are weaker than echo signals originating from reflectors with the same characteristics but located on shallower planes;
- a demodulator that converts the amplified RF signal into a single peak representing the signal of each reflector encountered by the ultrasound. This makes it possible to identify all points where a reflection has occurred and to quantify the echo amplitude;
- a scan converter that converts the time continuous input signal, sampling it at defined intervals and transforming it into a discrete numerical form that will be encoded according to the signal intensity with 16,64,256 levels of grey according to a format that can be represented on a monitor since the image is acquired along the lines that make up the scanning field while it is represented along horizontal lines on the monitor. This is achieved in two main macro phases where in the first phase, at the input, the scanning converter performs the analogue-to-digital conversion of an RF signal and stores the data in binary format on a memory matrix, and a second phase, in output, where it performs the digital/analogue conversion of the data stored on a memory matrix;
- a display/storage system that allows viewing of the tracing, usually by means of a monitor, and storing it on appropriate storage media for subsequent viewing.

A particular application of diagnostic ultrasound imaging uses Doppler measurement to detect and display fluid flow velocity. This is the physical phenomenon whereby a sound wave frequency that encounters a moving body undergoes a variation that is directly proportional to the speed of the body's movement itself.

The Doppler effect is therefore based on measurement of frequency variations between an incident beam and a reflected beam from a moving body (in medical applications moving bodies are represented in most cases by red blood cells, therefore by blood).

Consequently, the Doppler effect is the principle on which many ultrasound techniques in which movement in biological tissues are explored are based. Reflected echoes frequency variation is related to velocity and direction of a reflecting body. Received echo signals are compared to a reference value in order to establish a fluid flow velocity through the region. The flow velocity can be established by a measurement of the Doppler frequency shift of the echo signals received from the structure under examination.

There are two basic doppler acquisition systems:
- continuous wave (CW), which allows a study of flows morphology and movement;
- pulsed wave (PW), which also provides information on distance between a reflecting surface and the transducer.

Color-Doppler is based on same principle by integrating flow information and real-time two-dimensional image where, by convention, approaching flows have a red color and leaving flows have a blue color. As is known in prior art, the flow velocity can then be viewed by coloring in which different shading and color intensities represent flow rate and direction inside a grayscale image. If a turbulence is present, for example at the bifurcation of the vessel, there will be an alternating pattern of blue and red patches. It will thus be possible to distinguish the direction of flows in relation to the probe; these systems, moreover, help to evaluate the rate and the laminar or turbulent regime of flow itself.

It is clear how important it is to obtain a result that is as accurate as possible from the ultrasound machine since this can be used for a correct diagnosis by a doctor.

This highlights two main problem categories of these systems related on the one hand to the operation of the doctor or operator, and consequently to his experience with an ultrasound machine, which must operate on settings parameters in order to obtain a valid result and on the other hand to the system itself.

Ultrasound machine parameters that can be set by doctor or technician are, for example, gain controls and ultrasound focus settings in order to achieve the most uniform distribution of image brightness by amplifying signals from deeper layers, maximizing contrast and avoiding saturation. On the ultrasound machine there are commands that allow you to act on a scale setting used by TGC according to the individual work habits of doctor or technician to improve the representation of deep layers.

This parameter acts directly on signal background, understood as signal-to-noise ratio, generated by the electrical circuits in the production phase, reception and processing of ultrasound signal that would be manifested in the image as misrepresentation of flow signals in vascular areas by offsetting ecostructural characteristics that increases with excessive signal amplification or gain values, an example of misrepresentation is the Blooming artifact shown in FIG. 5E. Focuses setting allows to modify the number of active focuses, shape and thickness of the ultrasound beam, when not correctly set it affects the spatial resolution of the ultrasound image. Other settings that can be configured are the imaging frequency, where an increase in its value allows to optimize the resolution while a decrease in its value allows to increase the beam penetration. Another parameter on which the doctor or the operator can act is that relative to the compression curve that allows to vary the law of correspondence between the signal amplitude and the gray levels represented on a monitor. With a linear intensity/amplitude relationship, gray levels are directly proportional to the difference in acoustic impedance of examined tissues. In some cases this is not the optimal setting for a diagnostic need and therefore the doctor or operator are able to represent with greater evidence some acoustic impedance ranges than others of less interest, for example by compressing higher intensity echoes and allowing lower intensity echoes to be represented with a high number of gray levels. A sensitive parameter in clinical practice is the "pulse repetition rate" (or "flow sensitivity"), which controls the system's ability to acquire flows of varying velocity. If the pulse frequency is too high, sensitivity to slow flows decreases, resulting in a loss of corresponding signal.

Other critical categories belonging to the system, or the limits derived from this technology, mainly due to the interaction between ultrasounds and biological structures, will be highlighted in the following description of the possible artifacts that may arise in the result of an ultrasound examination. Critical issues of instrumental origin and/or those related to the experience of the doctor or the technician both in the phase of use of the ultrasound machine and in the configuration phase are reflected on the result produced by the ultrasound machine itself and are normally identified with the name of artifacts. By artifact we therefore mean false or distorted information generated by the ultrasound machine or by the interaction of ultrasounds with the tissues that overlap noise on the Doppler signal. In particular, the doctor's or technician's experience in using the ultrasound machine directly leads to a variable presence of a greater or lesser quantity of artifacts depending, for example, on probe positioning, on movements made by the probe itself and on speed with which it performs such movements.

Artifacts that can be found in a Doppler ultrasound imaging can be confusing or misleading in terms of flow information given that, for example, in a color Doppler ultrasound image, the artifact can be defined as the whole colored pixels that do not truly represent vascularization. As described above, three main factors are responsible for this issue: misconfiguration of equipment and inadequate signal acquisition due to human error, anatomical factors, and technological limitations. For example, wrong gain settings, wall filter settings, or velocity scale settings can cause loss of clinically relevant information such as presence or absence of flow in a vessel, flow direction and velocity, or tracing distortion displaying a situation that may significantly differ from the actual physiological situation. Referring to artifacts dependent on improper acquisition, motion artifacts are particularly relevant. These comprise, for example, those due to an improper insonation angle setting and those due to too fast signal acquisition, which are the most frequent mistakes causing flash artifacts. For the problem due to insonation angle, that is the angle between the operator's hand and the probe, when it is greater than 60°, the spectral curve amplitude is progressively reduced making the rate calculation progressively less reliable. On the other hand, when it is close to 90°, no signals are recorded, although flow can produce a low-amplitude signal. Below main artifacts found in a color Doppler ultrasound according to previously defined categories.

Artifacts Depending on Misconfigurations

Doppler Gain Setting Errors:

A proper gain setting is crucial for an accurate representation of the flow characteristics. For a gain setting too low, some relevant information may be lost, therefore the gain is adjusted frequently to maximize the trace visualization. On the contrary, higher gain degrades envelope signal, disrupting its representation on screen and simulating a spectral broadening that can give, for example, the appearance of flow turbulence.

Improper Angle Setting:

For insonation angle issue it is possible to set a correction parameter on ultrasound machine, however when the angle is completely wrong even this correction is useless. The occurrence of this type of artifacts may also depend on using transducers with very high frequency or a lack of gain adjustment.

Improper Filter Setting:

The filter phase is designed to remove low-frequency Doppler signals that come from echoes of slow-moving soft tissue, and the cutoff frequency of this filter is operator-selectable. If set too high, diagnostically relevant velocity information may be lost.

Artifacts Due to Spectral Dispersion:

Spectral dispersion can occur due to excessive system gain or from changes in grayscale sensitivity.

Anatomy-Dependent Artifacts

Flash Artifacts:

This artifact occurs as a sudden color blast extending to a more or less extensive scan field region. Color coding is completely artifactual and may be caused by too rapid transducer movements or by heart movements or arterial pulsatility causing slight movements of the reflective surfaces.

Pseudoflow Artifacts:

Pseudoflow represents a real fluid movement of a different from blood. These types of artifacts can be observed as a result of Doppler signal over-amplification, excessively low color coding (which can lead, for example, to signal appearance within cystic formations), contiguous moving structures, respiratory kinetics. May also occur due to the presence of mirror artifacts or shimmering.

Artifacts Depending on Technological Limitations

Directional Ambiguity:

Directional ambiguity may occur when the ultrasound beam intercepts the vessel at a 900 angle. Detected Doppler signals arise as tracking above and below the spectral baseline. Furthermore, at high gain settings, directional ambiguity is more evident and tracing is more inaccurate. When a color Doppler image is produced using a sector-type transducers, flow perpendicular to the beam is usually present along a small segment of a vessel parallel to the transducer surface while with using linear probes the issue becomes more marked.

Side Lobe Artifacts:

Electronically focus array transducers direct the primary beam to the interest area to be examined. However, due to the array element spacing weak secondary ultrasonic lobes can target areas unrelated to the primary one. The exact location of these lobes depends on transducer design itself. If these secondary lobes hit highly reflective surfaces (such as bone), the echo returning to the transducer may be detected on screen in conjunction with the primary beam echo.

Random Noise Artifacts:

In Doppler-type ultrasound machines, as in all electrical circuits, noise is proportional to gain. Random noise occurs, especially in cases where the gain is set too high, through the appearance of flash artifacts, every time a reciprocal movement probe-tissue occurs, or through the appearance/disappearance of color areas.

Twinkling Artifact:

This artifact type is visible in case of highly reflective structures and manifests itself as a fluctuating colored mosaic associated to the signal characteristic of background noise presence. Its apparition is strictly dependent on ultrasound machine configuration and is generated by a narrow band of intrinsic electronic noise called phase jitter.

In prior art, several signal processing techniques are known to be used to filter out unwanted signals within ultrasound imaging systems that are responsible for occurring one or more artifacts previously described. However, these solutions, implemented as part of the image display generation process within the ultrasound machine as a processing and/or filtering phase inserted upstream of image generation, show self-defeating effects, in a more or less relevant way, such as the loss of instrument sensitivity and/or relevant information for diagnostic purposes.

Moreover, the elimination of potentially different types of artifacts depends on different combinations of ultrasound machine parameter configurations as well as available processing and filtering enhancements depending on ultrasound machine model.

SUMMARY

The purpose of the present invention is to solve at least in part the above-mentioned instrumental or human-caused disadvantages by acting on ultrasound video produced by an ultrasound machine instead of acting on signal information and/or on image generation by means of an on-board filtering and/or processing block. It is possible to achieve this result through a denoising step on video generated by the ultrasound machine acting on 2D representation whose analysis aims to identify any artifacts present on video in order to remove them to minimize the effects due to non-optimal settings and/or operator experience and/or technological limitations, providing as a result a video artifact-free or with a significant reduction of them.

Denoising is therefore the analysis of Doppler ultrasound videos, through the steps of the method described below, aimed to identifying the presence of any possible artefacts within the video that may overlap or flank the real signal in order to remove them, obtaining as a result a video free of such alterations that may prevent or mislead the diagnostic phase. Further terminology contained in the present invention that deserves a definition and help to contextualize its use within the of the description are:

Doppler activation, i.e. the set of pixels bearing doppler signal and doppler artifacts such as colored pixels;

ultrasound signal, i.e. the set of pixels bearing a non-Doppler ultrasound signal such as, for example, gray-scale pixels belonging to the external area from which the Doppler signal is collected;

doppler signal, i.e. the set of pixels bearing real doppler signal that are therefore indicating the presence of vascularization.

The computer-implemented denoising method of the present invention, starting with a video decomposition into individual frames using standard video segmentation techniques comprising the steps of:

Acquiring n frames from ultrasound video;

Identifying for each of the n frames a first pixel category representative of first pixels of the n-th frame containing ultrasound signal; and a second pixel category representative of second pixels of the n-th frame containing doppler activation;

Generating for each frame belonging to said plurality, a first set of image data in order to associate to each pixel position of the corresponding frame at least a first or a second category so as to categorize the pixels of the corresponding frame and identifying for each frame the pixels containing doppler activation;

Generating at least a persistence sequence associated to a frame portion containing identification data ordered according to the frame sequence such that adjacent identification data refers to adjacent frames, wherein each identification data assumes a first value if the corresponding frame portion contains doppler activated pixels or a second value different from the first value if the corresponding frame portion does not contain doppler activated pixels;

In said persistence sequence, calculating the length of each persistence sub-sequence comprising consecutive identification data having the first value;

Calculating a reference threshold based on length distribution of said persistence sub-sequences referring to whole identification data for n frames;

Identifying for each of the n frames a second set of image data (SEED) in order to associate to each pixel position in the corresponding frame:

the information that said pixel position belongs to said second category when the frame n corresponds to one of said persistence sub-sequences having a length greater than said threshold so as to be representative of a pixel with real doppler signal; or the information that said pixel position belongs to said first category when the frame n corresponds to another one of said persistence sub-sequences having a length shorter than said threshold so as to be representative of an artefact.

This method is based on doppler signal persistence in the n frames and identification data which, although belonging to a first value indicating the presence of doppler activation, are considered as artefacts, are relatively weakly persistent in the n-frames and as identification data belonging to a first value indicating the presence of doppler activation, the data more persistent in the n frames.

The step of generating a temporal persistence sequence of Doppler activation is applied to portions of each frame. According to an embodiment, such region is the single pixel of the frame and as many persistence sequences are generated as there are pixels of the frames of the video format, i.e. the pixels matrix that constitutes the frame e.g. 800×566 format. Each persistence sequence contains identification data for each frame of the video. According to a further embodiment, the portion of the frame to which the persistence sequence refers is a connected component of pixels with Doppler activation.

In this second case, particularly, it is necessary to perform the step of executing a search algorithm for connected components comprising pixels of said first category on a frame n and a frame n+1 to define said frame portions and wherein the step of generating a persistence sequence comprises the step of comparing a first parameter of a first connected component of frame n and a second parameter of a second connected component of frame n+1 and associating the second connected component with a first persistence sequence of the first connected component or generating a second persistence sequence for the second connected component based on the step of comparing, in order to obtain a tracking of the connected components between the n-frame and the n+1-frame, said parameter preferably being a centroid and/or a parameter representing overlap of the first and second connected components and/or a parameter representing similarity of shape of the first and second connected components and/or a parameter of size or dimension of the first and second connected components.

In this way, the connected components enable to perform tracking or tracing of Doppler-activated areas and the processing accuracy is increased in the presence of Doppler signal areas that change during Doppler data acquisition.

According to a preferred embodiment when the frame portion is the pixel, the method comprises the step of performing a segmentation algorithm on at least one n-th frame on the basis of the second image data set (SEED) related to the n-th frame to expand said second image data set with further pixels containing doppler signal having previously been eliminated pixels representative of artefacts. Particularly, also on the second set of data of each frame with reference to the pixels representative of the real doppler signal is executed the research of connected components and, for each frame, the connected components of the video frame and those of the pixels of the real doppler signal pixels of the real doppler signal are overlapped and, having defined an overlapping threshold e.g. 90%., the connected components of the video frame that pass the overlap test and are disabled are retained, e.g. modified, the pixels of the doppler activated connected components of the video frame that do not pass the overlap test and are therefore considered artefacts.

In particular, it was found that the second set of image data tends to underestimate the extent of the representative area of pixels with real Doppler signal (i.e. excluding pixels related to artefacts). In order to increase the precision of the processing of the original frames, a segmentation algorithm is therefore applied to expand the second set of image data so as to annex additional pixels with doppler signal having been previously eliminated, as indicated in the previous paragraphs, the pixels considered representative of artefacts.

According to a preferred embodiment each frame acquired can be represented by a three-dimensional matrix where a first dimension represents the number of pixels on vertical axis, a second dimension represents the number of pixels on horizontal axis and finally a third dimension represents the number of channels (R, G, B) describing therefore each pixel by a triplet of values.

According to an embodiment of the present invention, identification of colored pixels of step 2 of denoising method, representing pixels containing doppler signal, can be achieved by dividing R, G, B values of pixels composing the frame into clusters and selecting those pixels that do not fall into a cluster that identifies ultrasound machine monochromatic scale.

According to another embodiment of the present invention, the identification of the colored pixels of step 2 of the denoising method can also be achieved by selecting pixels wherein the difference between intensities of R and G, G and B or R and B channels is greater than or equal to a predefined threshold.

According to a preferred embodiment, the threshold is computed as the 90th percentile of the distribution since the purpose is to obtain a minimum activation length value of Doppler signal such that activation sequence lengths greater than this threshold are assumed to correspond to a real signal, while activation sequence lengths less than the threshold are assumed to be artifacts.

According to another preferred embodiment the threshold is computed as the 98th percentile when the minimum value activation length of the Doppler signal is derived by tracking the temporal persistence of closed and separated Doppler regions, i.e. connected components, contained within the frames.

According to another embodiment, the threshold for both embodiments of the frame portion is computed as the sum of the average with the double standard deviation of the lengths of the representative doppler activation sub-sequences over the logarithm to compensate for distribution asymmetry.

According to a preferred embodiment in the step of localization of the real signal the visible result in denoised frame may contain Doppler signal pixels with values of color channels [R, G, B] of the original frame while other pixels will assume an average value on the three channels falling into the gray scale representation.

According to a preferred embodiment in the region growing step a morphological erosion method is used, followed by a morphological dilation method, with a kernel diameter or side of 5 pixels and a threshold value of 10%.

According to a preferred embodiment, there is a step of displaying the n-th frame in which pixels corresponding to the real doppler signal are retained and pixels corresponding to an artefact are modified, e.g. presenting a predefined grey scale value so as not to be displayed as Doppler-activated pixels.

BRIEF DESCRIPTION OF THE DRAWINGS

Preferred embodiments of the present invention will be described below, for purposes of example only, with reference to the attached drawings, wherein:

FIGS. 4A-4D show four sub-steps of step 7 of the method described in the present invention where starting from the top left and proceeding clockwise it is possible to see a connected component identification, the dilation operation result, the colored pixel computation and the final result of the frame at the end of the execution of the steps forming the method described in the present invention.

DETAILED DESCRIPTION OF THE EMBODIMENTS

Figure 1:
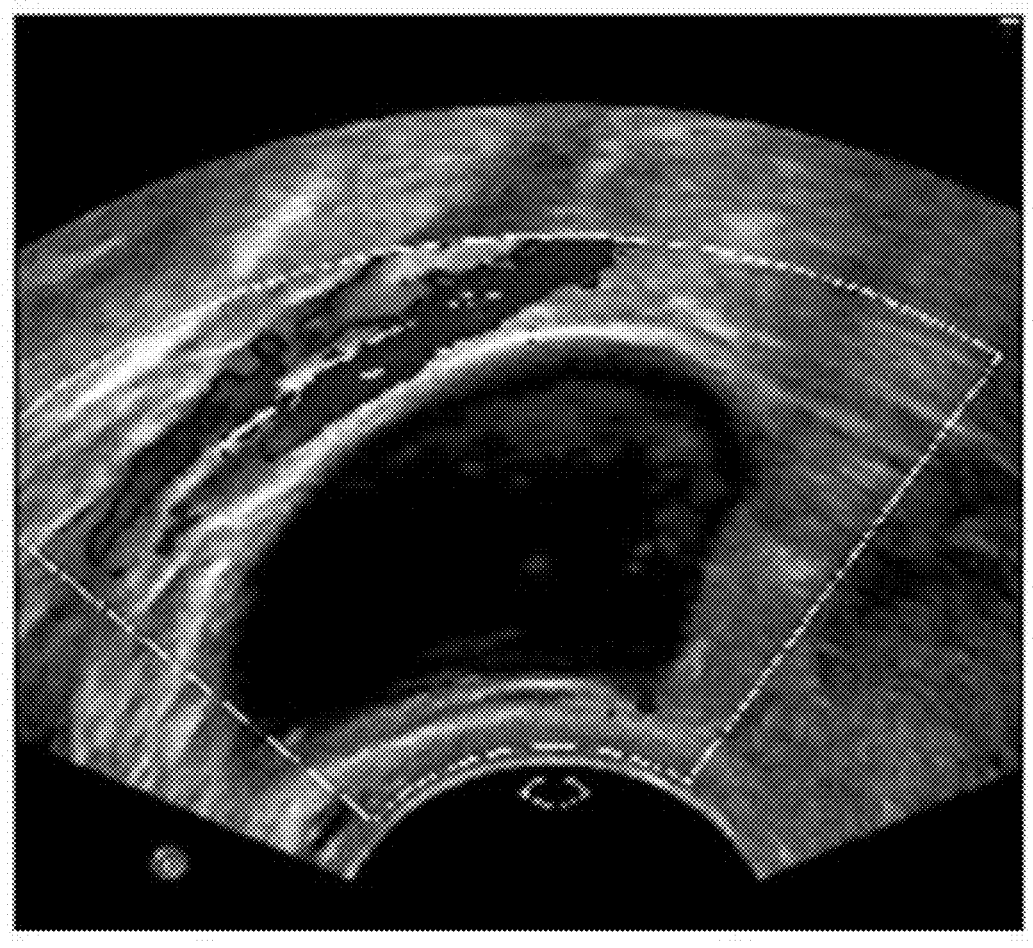
FIG. 1 shows a frame example extracted from an echodopler-type video.

FIG. 1 shows an example of a single frame belonging to an echodoppler video in which it is possible to identify the real Doppler signal presence in the upper left image region and the artifacts presence within the dark area in the image lower part that in the specific case represents a cyst.

In the following description will be further analyzed in detail, according to an example of a preferred embodiment, steps comprised by the present invention's method of analyzing ultrasound video that is designed to remove multiple artifacts that may flank and/or overlap a real signal.

Echodoppler Video Input Acquisition

In this step the ultrasound video is acquired in the form of a packet of frames, or it is possible to acquire the video directly which will be unpacked by the algorithm itself, which the analysis of the of the single frames carried out by the algorithm will lead to an evaluation of temporal persistence through the succession of all the frames. Each frame can be represented as a three-dimensional matrix where first dimension represents the pixels number on vertical axis, second dimension represents the pixels number on horizontal axis, and third dimension represents color channels number [R, G, B]. The value of each pixel can therefore be described by a triplet of values in a range 0, 255.

Pixels Identification Containing Doppler Signal In order to split the real Doppler signal from noise caused by artefacts, it is necessary to isolate the entire Doppler activation (real+artefact/noise) within each frame, for all frames comprised in the echodoppler video. The result of this operation will lead to the identification, for each frame, of two sets of data, the first one containing the Doppler activation (coloured pixels), the second one containing the ultrasound signal (in grey scale, or monochrome).

The union of the two sets identified above for all the frames comprised in the ultrasound video can be represented through a matrix of dimensions n. frames×n. pixels on vertical axis×n. pixels on horizontal axis.

In detail, in this step, coloured pixels, i.e. pixels containing Doppler activation, are identified for each frame and thereafter an image data set is generated in which pixels containing Doppler activation (coloured pixels) value 1, while other pixels value 0 (greyscale or monochrome pixels).

Coloured pixels can be identified by selecting those pixels for which modulus of the difference between the intensities of the R and G, G and B or R and B channels is greater than or equal to a predefined threshold. This threshold according to a preferred embodiment is identified as |R–G|>=30 V|R–B|>=30 V|G–B|>=30. The reasons are due to computational speed requirements and to the lack of necessity to assign a known colour to coloured pixels carrying the Doppler signal in order to identify in which of the two data sets a pixel under examination falls. An alternative way to identification through the difference in channel intensity is a machine learning method.

According to this method, all pixels in a frame are split into separate sets by colour and then merged into two subsets: a first one comprising all colour sets found in the Doppler spectrum (coloured pixels), and a second one comprising colour sets specific to greyscale ultrasound. The basis of these operations is the a priori knowledge of specific colour tones of Doppler signal display in a given video. This colour label assignment for each pixel can be done by an unsupervised clustering operation, or with the help of a classifier/neural network trained to extract main colours within an image.

In one of its implementation, this method comprises:

(1) the initialisation of the unsupervised clustering method, such as k-means, to the distribution of pixel values of pixels [R, G, B];

(2) once the pixels have been grouped in clusters, the centroid is calculated, defined as the central [R, G, B] triplet of the cluster—the most representative triplet of the cluster;

(3) a colour label is assigned to each of the centroids and by extension to all the pixels that compose the given cluster; this operation can be done by calculating the distance in colour space (ciede2000) of each centroid from known colour labels and selecting as label the one that is at a shorter distance from the centroid.

(4) all pixels with a colour label different from a grey value (comprising whites and blacks) are placed in the same set, and pixels with a greyscale value in another set.

These methods require computational power and, in case of unsupervised methods, also a priori knowledge of the colour shades that the doppler signal can assume in the video for the creation of the labels. Consequently, there is a dependency on the characteristics of the colours that the doppler signal can assume in the video. Consequently there is a dependence on features and settings of the ultrasound machine used and the type of doppler, colour doppler rather than power doppler. This method is preferable when, for example, colour information is to be retained in the analysis of artefacts, e.g. to be able to observe pixels filtering showing the approaching direction (conventionally in red).

Figures 2A, 2B:
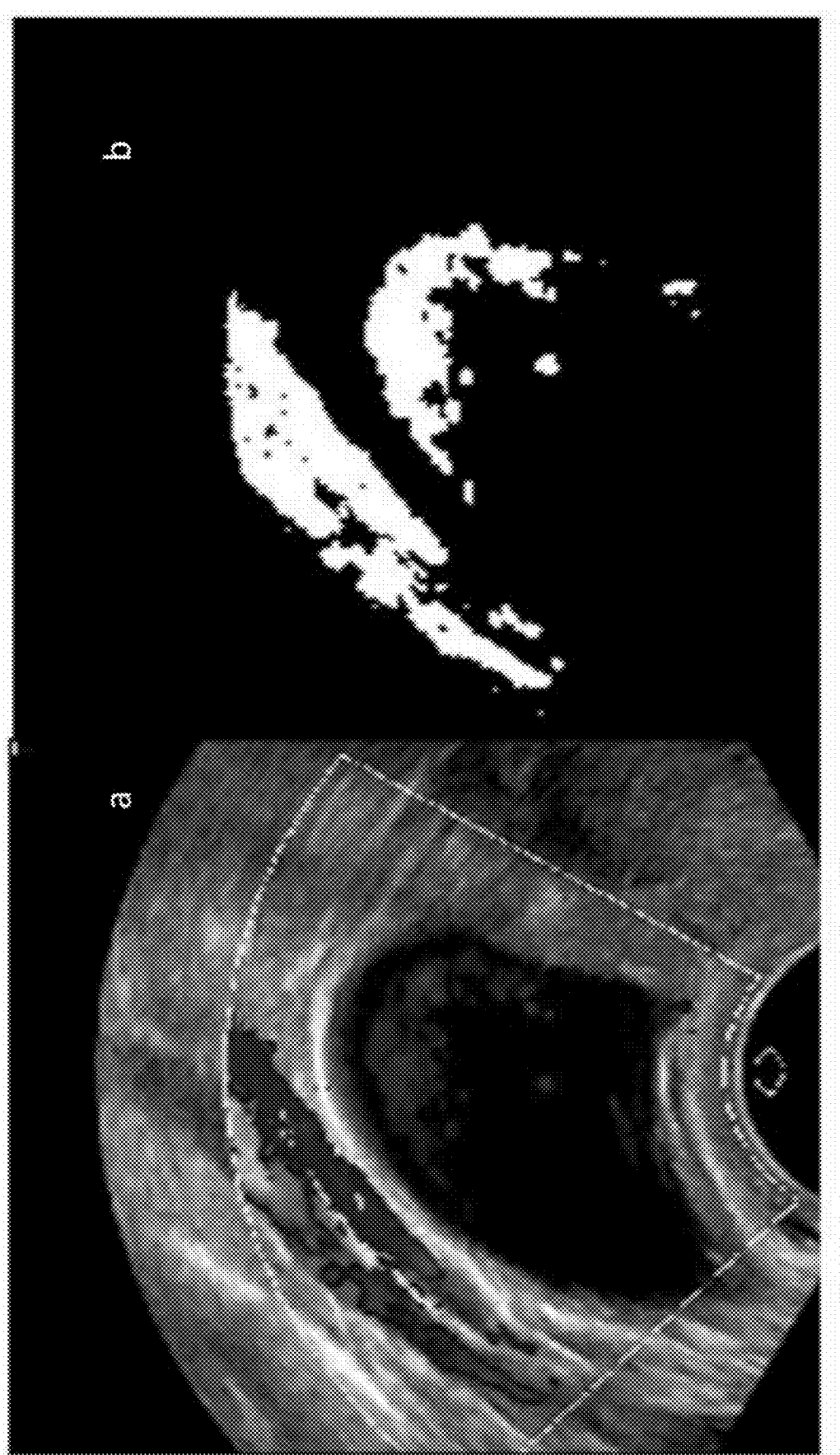
FIGS. 2A-2B show an example of identifying colored pixels on the left and the corresponding set of image data e.g., binary mask on the right.

An example of a coloured pixel identification step using the intensity difference identification method is shown in FIGS. 2A-2B. The left side of the image shows the frame under examination, while the right side of the image shows the corresponding element belonging to the image dataset where light areas corresponding to coloured pixels identified in frame and dark areas for other pixels are visible.

Activation Sequence Identification (Second Category)

The assumption underlying the method of the present invention is that the doppler artefacts, the noise, have a a temporal persistence, i.e. a duration expressed in terms of frames, which is shorter than the real signal for a given echo-Doppler video under examination.

In order to quantify the doppler signal temporal persistence, the "doppler activations" lengths of each pixel are calculated through two operations.

Figure 6:
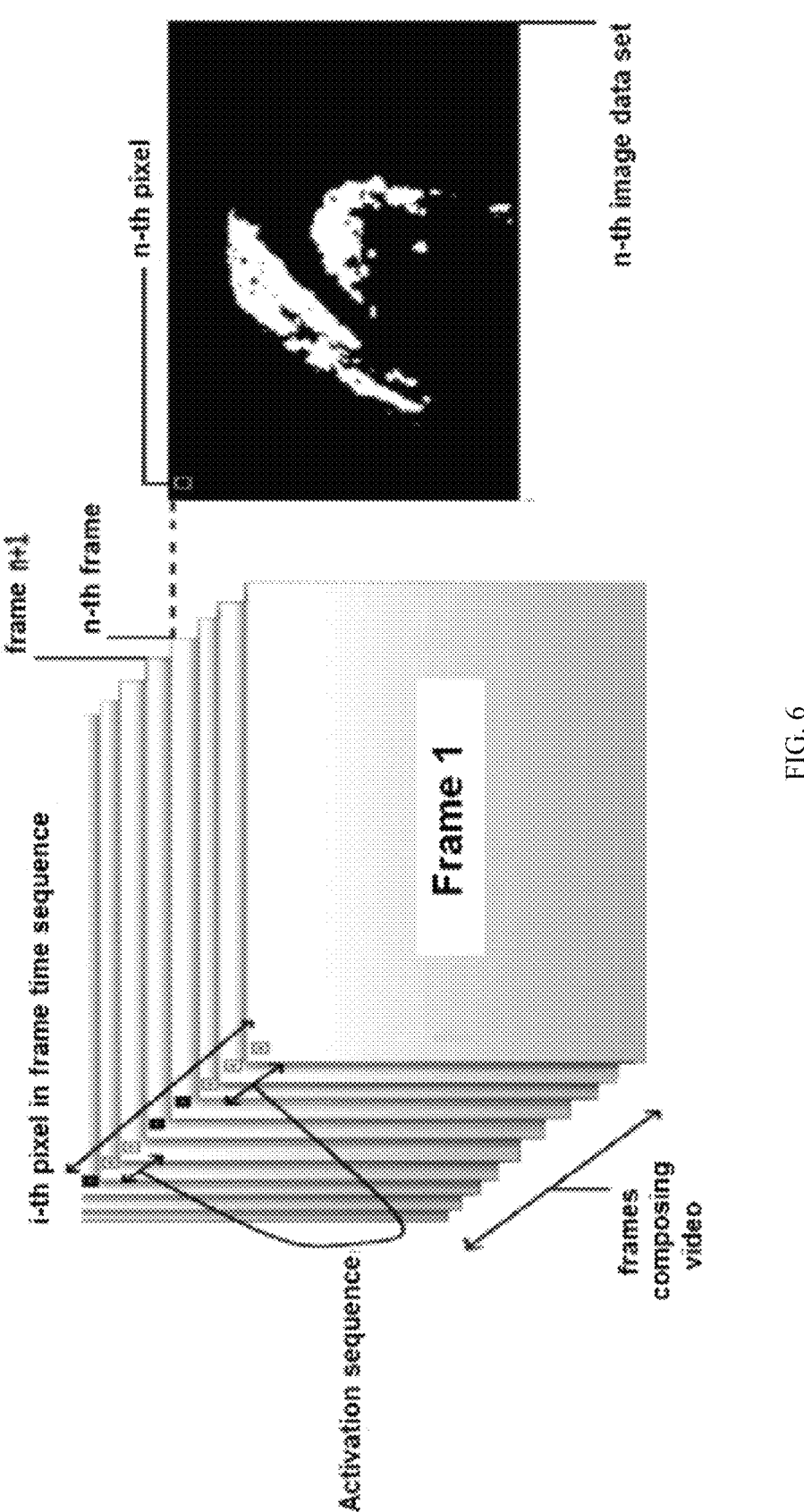
FIG. 6 shows a schematic overview of the plurality of frames in a temporal sequence with the corresponding image data sets associated with the respective frame.

According to a first embodiment, the input of this step is the matrix of binary images of size n (frames)×n pixels vertical axis×n pixels horizontal axis created in the previous step. Firstly, for each pixel in the matrix, an activation vector is populated, defined as a vector of length n (equal to the number of frames of the video) and cardinality [0,1] (values that can be assumed by each pixel according to whether they are coloured or not), where each vector element will be valued with the corresponding pixel value of the frame, for each frame. Said values correspond to a first category of information, i.e. 0 for pixels without doppler activation and a second category i.e. 1 or 'not 0' for pixels with doppler activation (FIG. 6).

Subsequently, for each vector, the activation sequence lengths are calculated (consecutive sequences of 1 or 'not 0'—second category). sequences (consecutive sequences of 1 or 'not 0'—second category), and the number of frames in which each sequence persists (or disappears) the doppler without interruption.

According to an application of these operations, the result obtained can be described as a matrix of size n pixels on vertical axis×n pixels on horizontal axis and in which each matrix element is a persistence vector of different length $1$. The reason for the different persistence vectors length is due to the number of activation/deactivation detected for each pixel. Each vector element will be a pair of values (count, value), where value refers to the value (0, 1) of the sequence, while count refers to the number of frames in the sequence.

Assuming, for example, that a video is split into 20 frames, and considering a pixel with coordinates $x_1$, $y_1$, whose vector of activations, as described above, is defined as:

[0,0,0,1,1,0,0,0,0,0,1,1,1,1,1,0,0,1,1,1].

The corresponding duration (or persistence) vector will have length $6$ (equal to the number of activation/deactivation sequences in the activation vector) and will be composed of the following pairs (count, value):

[(3, 0), (2, 1), (5, 0), (5, 1), (2, 0), (3, 1)].

According to another preferred embodiment the doppler signal temporal persistence can be made by tracking the temporal persistence of closed and separated doppler regions, i.e. connected components of doppler regions, inside the frame instead of making it on a single pixel.

Inside a frame belonging to a doppler type ultrasound video it is possible to identify, within the area of interest that is the object of the ultrasound scan, areas defined by grey scale (or monochrome) pixels, which will be referred to as non doppler pixels, representing the doppler type signal and areas defined by coloured pixels, which will be referred to as doppler pixels, representing the doppler type signal. The doppler pixels can be further distinguished according to doppler pixels representing real doppler activation, to which reference will be made as real doppler pixels, and doppler pixels representing artefacts, referred to as artefact doppler pixels.

By connected components it is meant the identification of distinct objects existing in an image, where each of said objects has the characteristic of being formed by a set of pixels that satisfy the same adjacency relation, called connection.

It is possible to identify connected components within a frame by means of algorithms capable of identifying the pixels' properties within the frame, labelling them and determining whether they should be grouped into a single set that will be represented as an object with a certain shape. These algorithms allow, for example, to distinguish pixels belonging to the category of real doppler pixels from pixels belonging to the category of artefactual doppler pixels on the basis of criteria such as morphology, centroid distance or overlapping. This family of algorithms allows, once the connected components in a given frame have been identified, to track them in subsequent frames in such a way as to be able to distinguish objects belonging to the same connected component even when they become distorted or fragmented in subsequent frames. In addition, if it allows to identify those connected components that artefacts by filtering them out when they are no longer visible in subsequent frames.

The underlying necessity arises from the different implementation of a doppler-type ultrasound video. In fact, in the case of static videos, the probe does not move and the region of interest and the vessels always cover the same region along the sequence of frames that constitutes the video. In this case, temporal persistence can be determined pixel by pixel by considering the same row and column values in the binary image matrix for all frames of the video. Conversely, in the case of making a video in which the probe makes movements during the acquisition phase, the background is no longer static along the sequence of frames that constitute the video and single pixels do not maintain a fixed correspondence between consecutive frames. In this case, temporal persistence can be performed by considering the connected components existing along the sequence of frames composing the video.

Once the whole Doppler activation has been isolated (considering both the real and the artefact/noise signal), within each frame as described in the previous paragraph "Pixels identification containing doppler signal", the connected components are identified through two main steps.

In a first initialisation phase, all connected components (objects) located in the first non-empty binary mask associated with the corresponding frame of the video are identified.

For this mask, the centroid of the rectangular bounding box, or of the connected component itself, is calculated for each component identified, and a vector $V_0$ associated with the component is initialised with the following information:

a unique identifier the centroid of the rectangular bounding box or of the connected component itself;

the coordinates of the rectangle bounding the component within the current mask;

a vector $V_1$ of size equal to the total length of the frames that will contain the indication of the coordinates (rows and columns) occupied by the object when present in the related frame, where in that initialisation phase, the coordinates (rows and columns) occupied by the object in the current frame are stored as the first element;

th boolean information $B_{V_0}$ to indicate whether said object is still tracked or not is initialised to a value which marks the object as tracked. Examples of values are T, 1, Y,S, etc.;

A progressive $I_{VO}$ indicating the number of frames in which the object is no longer visible after its first appearance;

A vector $V_2$ of dimension equal to the total length of the frames constituting the video where each element, when set, shows the presence of the object in the related frame.

Figure 7:
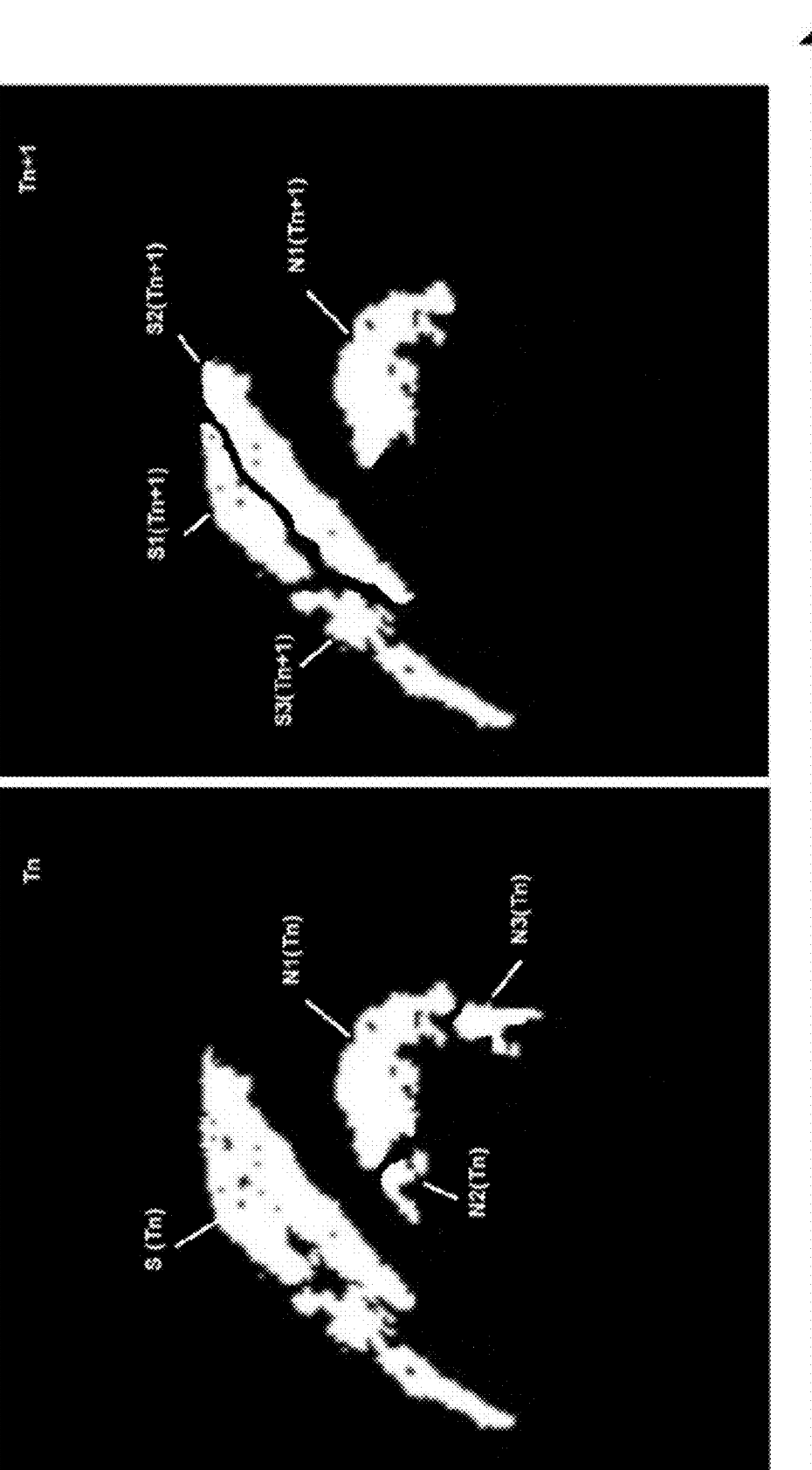
FIG. 7 shows an example of signal and noise temporal variation between two consecutive frames of an echodopler-type video.

With reference to FIG. 7, assuming that the image on the left represents the first non-empty binary mask, the initialisation phase will detect the presence of 4 components within the mask: S(Tn), N1(Tn), N2(Tn), N3(Tn). For each of these components a vector is initialised, respectively the vectors $V_{S(Tn)}$, $V_{N1(Tn)}$, $V_{N2(Tn)}$, $V_{N3(Tn)}$, containing the information as described above.

For each binary mask after the one identified by the initialisation phase, it shall be determined whether the objects existing in the current mask Tn+1 represent new objects rather than being tracked as one of the moving objects identified in the previous mask Tn. To achieve this result it will be necessary:

locating all objects in the current mask Tn+1;
determining for each object belonging to the mask Tn+1 the centroid and the coordinates of the rectangle delimiting the component inside the mask Tn+1;
for all possible pairs of objects between Tn and Tn+1 the distance between the centroids and the overlapping value between the coordinates are calculated.

Once the above values have been calculated, an OTn+1 object located in the mask Tn+1 shall be identified as an object in the previous mask Tn if at least one of the following conditions is satisfied:

exists an object OTn whose pair $(OT_n, OT_{n+1})$ whose overlapping value is at least equal to a predetermined threshold value Ts;
exists an object OTn whose pair $(OT_n, OT_{n+1})$ whose distance between coordinates is at most equal to a threshold value Td;

Additional comparison criteria can be used to determine if an object in a given mask can be identified as the same object as the previous mask, such as: similarity of shape features and overlapping object masks. According to an embodiment of the algorithm, the difference in pixel size of object $OT_n$, and object $OT_{n+1}$ is less than a given threshold Tm.

If the object $OT_{n+1}$ is identified as a tracked object in the previous mask the related initialization vector is updated with the properties of the object $OT_{n+1}$:

the vector $V_1$ is updated by adding a new element containing the coordinates (rows and columns) occupied by the object $OT_{n+1}$ in the current frame;
the vector $V_2$ is updated by setting the value of the element corresponding to the frame under examination.

If multiple objects in the current mask Tn+1 are identified as the previous mask's tracked object, the $V_1$ and $V_2$ vectors are updated for each of them with their respective properties.

In case the object $OT_{n+1}$ is identified as a non tracked object in the previous mask, the new object is tracked by defining a new $V_O$ vector in the same way as described during the initialisation phase.

The objects existing in the binary mask $T_{n+1}$ that no longer have a match in the binary mask $T_{n+1}$ are also updated as follows:

the boolean property that specifies whether the object is tracked or not $B_{VO}$ is set to a value indicating that the object is no longer tracked. Examples of values are F, 0, N, etc.

the progressive Ivo representing the number of frames after its appearance in which the object is no longer tracked is increased by 1. A tolerance threshold whereby an object even if it has disappeared for a certain number of frames is tracked for a given number of frames.

According to an embodiment, a tolerance threshold is defined to consider the possibility that an object may disappear for a given number of frames and then re-appear in subsequent frames. This threshold allows this event to be handled so that the temporarily disappeared object is considered as a single tracked object instead of two separate objects. According to an embodiment the threshold value is 0, therefore the event of disappearance and re-appearance of an object throughout a frame sequence is handled as two separate objects.

FIG. 7 shows an example of signal and noise temporal variation between two consecutive frames.

According to the previous description for the identification of connected components and assuming that the binary mask $T_n$ is the first non-empty mask, then:

during the initialisation phase, 4 vectors V01, V02, V03, V04 will be defined, associated respectively with objects S(Tn), N1(Tn), N2(Tn), N3(Tn) and set to values with their respective properties as described above;
in the subsequent mask Tn+1 the signal is degraded causing the appearance of new objects [S1(Tn+1), S2(Tn+1), S3(Tn+1)] and the disappearance of others [N2(Tn), N3(Tn)] compared to the situation existing in Tn;
at the end of the tracking of the subsequent mask Tn+1:
objects S1(Tn+1), S2(Tn+1), S3(Tn+1) will be tracked as connected components of the object S(Tn) and their properties will be updated on vector $V_{01}$ initialized at time T;
the object N1(Tn+1) shall be tracked as a connected component of the object N1(Tn) and its properties will be updated on vector $V_{02}$ initialised at time T;
objects N2(Tn), N3(Tn) in the mask Tn that no longer have a match in the mask Tn+1 will be updated as no longer tracked.

Reference Threshold Computation on Length Distribution of Activation Sequences

The purpose of this step is to obtain a minimum Doppler activation length value, so that activations longer than the threshold are considered as belonging to the real Doppler signal, while activations shorter than the threshold are associated with artefacts. This step begins with the n-pixel dimensionality set of duration (or persistence) vectors calculated in the previous step. In this step, however, only activation length values will be taken into account, and deactivation lengths will be ignored.

Going on with this example defined in previous step, where we found a persistence vector relative to pixel $x_1$, $y_1$ along the 20 frames that make up the ultrasound video:

[(3, 0), (2, 1), (5, 0), (5, 1), (2, 0), (3, 1)].

Only activation lengths will be considered, i.e.

[(2, 1), (5, 1), (3, 1)], and from these it is possible to define the set of durations as:

[2, 5, 3].

This procedure is carried out for all pixels that compose the frame. The reference threshold is calculated on the distribution of all activation durations for all pixels as a 90 percentile value or as (mean+1.282*standard deviation) for a normal distribution.

The threshold is calculated as the 98th percentile when the minimum doppler signal activation length is obtained by tracking the temporal persistence of closed and separated doppler regions within the frames.

Real Signal SEED Localization

Once a threshold has been defined, it is necessary to locate for each frame the real signal coordinates, the Doppler signal seeds.

For each pixel, the previously calculated vector of activation sequences is taken into account and compared with the threshold value as follows:

sequences with a length greater than or equal to threshold are kept 'on' (keeping the pixel value=1 in the activation vector sequence);

shorter length activation sequences are "switched off" (by setting the pixel value=0 for those activation sequences that although "switched on" do not reach the threshold value to be considered as belonging to the real doppler signal).

Proceeding with the example defined in previous steps, and assuming that previous step resulted in a threshold value of 4, it can be seen that in vector of activation lengths of the pixel $x_1$, $y_1$:

[(3, 0), (2, 1), (5, 0), (5, 1), (2, 0), (3, 1)]

only a sequence has a duration exceeding the threshold: (5, 1).

Therefore the activation vector that was originally calculated as:

[0,0,0,1,1,0,0,0,0,0,1,1,1,1,1,0,0,1,1,1]

at the end of this step will become

[0,0,0,0,0,0,0,0,0,0,1,1,1,1,1,0,0,0,0,0].

as defined above.

At the end of this step a matrix will be generated with dimensions n frames×n pixels on vertical axis×n pixels on horizontal axis, where for each frame each pixel will have value 1, if relative activation sequence was at least equal to threshold value, 0 otherwise.

Real Signal Localization

This step takes into account the matrix of dimensions n frames×n pixels on vertical axis×n pixels on horizontal axis defined in the identification step of pixels containing doppler signal, where for each frame of the matrix, we will use the image data set, e.g. a binary mask, defined in previous step to isolate the real doppler signal in the corresponding original frame of video (obtaining a denoised frame). For each frame, [R, G, B] values of pixels belonging to original frame will then be kept as real signal by considering pixels coordinates with value at 1 of the image dataset obtained in previous step and taking the relative triplet of [R, G, B] channel values corresponding to each coordinate in the original frame, or by multiplying the binary mask to the original frame.

A possible denoised frame view is that the doppler signal pixels hold [R,G,B] channel values of the original frame and are therefore coloured, while other pixels assume the average value of the three [R,G,B] channel pixels in original frame and are therefore greyscaled.

Figures 3A, 3B:
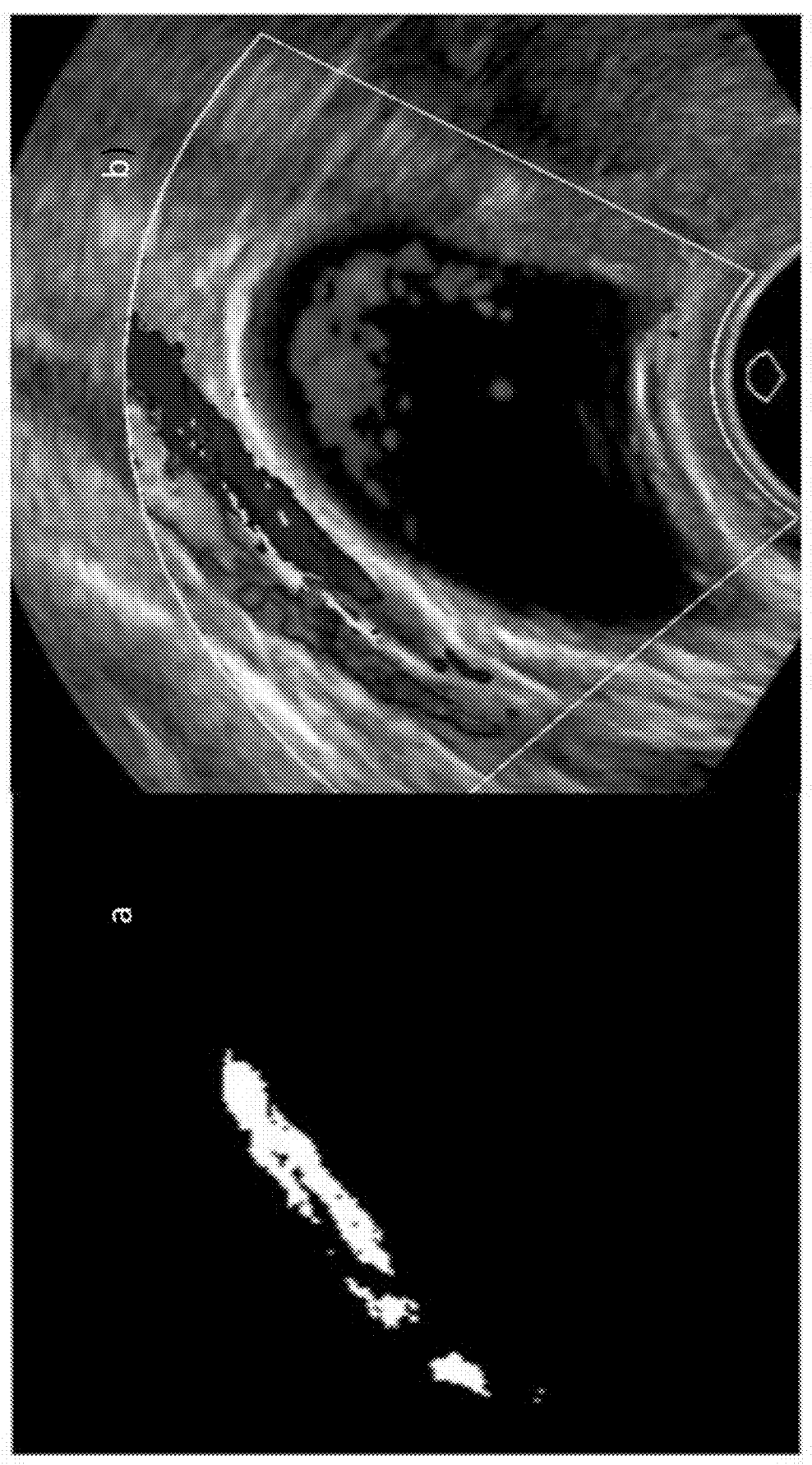
FIGS. 3A-3B show an example of SEED on the left related to the frame on the right.

FIG. 3A shows an example of a signal SEED for a given frame obtained preserving only the activation sequences of pixels of length at least equal to the threshold (second category pixels). FIG. 3B shows the frame resulting from the application of SEED to the original frame in FIG. 1. It is possible to see coloured pixels corresponding to real signal while artefacts have been masked in greyscale.

Segmentation and Expansion

Previous real signal localisation step returns pixels coordinates containing the real doppler signal. However, real signal region returned may not be correctly estimated, but underestimated. For example as a result of removing artefacts overlapping the signal, which also caused the removal of pixels belonging to a real signal. Other examples that may involve pixels belonging to the signal being removed could be due to probe movement by an operator, which caused the vessel's peripheral pixels to become thinner in subsequent frames, or the pulsation of signal itself.

In order to correctly identify the signal region edges identified in the seed localisation process, starting from each seed (such as the signal areas/coordinates recognised at the end of previous step) the connected Doppler activation components from original videos overlapping each seed are attached to signal areas/coordinates. This is performed for each frame according to the following operations of a first segmentation algorithm, for example:

a. The corresponding activation image data set is selected, in which values=1 denote the coloured pixels, and values=0 the others (the result obtained in step 2 of this method). It should b noticed that from this image data set, pixels corresponding to artefacts have not yet been "switched off" (FIG. 2B).

b. The morphological erosion operation is applied to the image dataset in order to separate the main connected components of the real signal from those related to artefacts as much as possible. In this embodiment erosion is applied with a circular kernel of 5 pixel diameter (FIG. 4A).

c. In the image data set of point b, the connected components are identified and labelled, i.e. each macroscopic component formed by n pixels>1 adjacent and connected (FIG. 4A—connected components with their colour). connected components with the relative colour).

d. The connected components of FIG. 4A are selected on the basis of the image data set in which only the activation sequences of the pixels with a length at least equal to the threshold are preserved (second category pixels—FIG. 3A). For example, based on the data overlapping the data of FIG. 3A on those of FIG. 4E, only the brightest area indicated by the arrow is retained as that with a percentage of pixels overlapping the activated pixels of FIG. 3A above a predefined threshold.

e. For each connected component selected on the basis of the second category pixels (FIG. 3A) the morphological dilation operation is applied to the same extent as the previous erosion application (recovering the erosion as its inverse operation). (recovering erosion as its inverse operation). In the present embodiment (FIG. 4B), the expansion is applied with a circular kernel of 5 pixel diameter.

When expanded image needs to be displayed on a screen, the following steps are carried out starting from FIG. 4B:

for each expanded connected component, count how many pixels survived to the filtering it contains (pixels that contain the real signal, according to the previous step);

if the number of coloured pixels is greater than or equal to a given threshold, in the new denoised frame, the colour is extended to the whole component, assigning to the pixels the corresponding [R, G, B] values in the original frame. In this embodiment, an optimal threshold has been set to 10%.

According to an alternative embodiment, the area of FIG. 3A is expanded as follows (not shown):

image data in FIG. 3A (second category) are overlapped with the related original frame (FIG. 1) in order to define a seed;

a segmentation algorithm is applied to original frame, based on seed, e.g. region growing to identify the largest area of which FIG. 3A is the seed.

Even in this alternative way, it is possible to obtain a larger area representative of the doppler signal in the original frame, since artefacts have been previously removed, in particular motion artefacts, and a doppler area with an underestimated extension has been identified, i.e. FIG. 3A.

Finally, FIGS. 5A-5E show some embodiments of method described in the present invention for removing artefacts from frames of an ultrasound video by placing original frame side by side with its denoised frame.

On the left is shown the frame before denoising was applied, on the right afterwards. Note that coloured pixels considered "artefact" have been replaced by greyscale pixels. These five videos were selected because they contain artefacts of different type, they show different anatomical objects within them, and they have different characteristics. In its original size, each frame is 800×566 pixels. In all, coloured pixels were identified as those pixels showing a difference in intensity between R, G, B channels of at least 30 points. The selected activation threshold is 90% of all activation lengths for each pixel in that video.

Figure 5A:
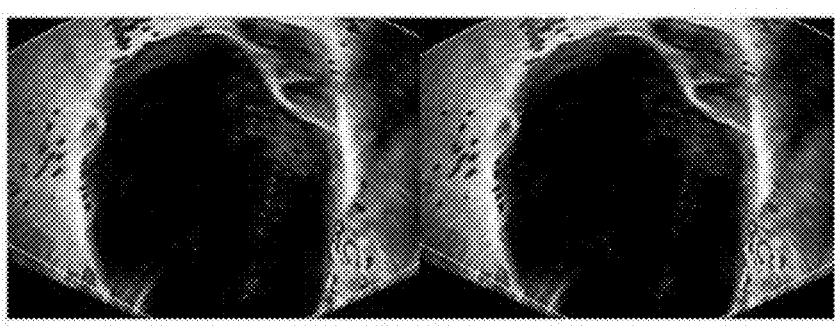
FIGS. 5A-5E show on the left examples of frames extracted from an ultrasound video and on the right the corresponding frame at the end of the denoising process operated by the method of the present invention for some types of artifacts detectable in an ultrasound video.

FIG. 5A: example of flash artefact removal. This video is composed of 113 frames, recorded at 57 fps; the algorithm has set an acceptance threshold of 17 consecutive activation frames.

Figure 5B:
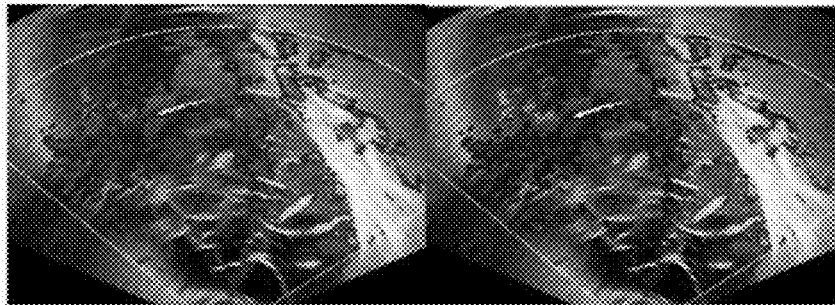

FIG. 5B: example of flash artefact removal. This video is composed of 70 frames, recorded at 13 fps; the algorithm has set an acceptance threshold of 11 consecutive activation frames.

Figure 5C:
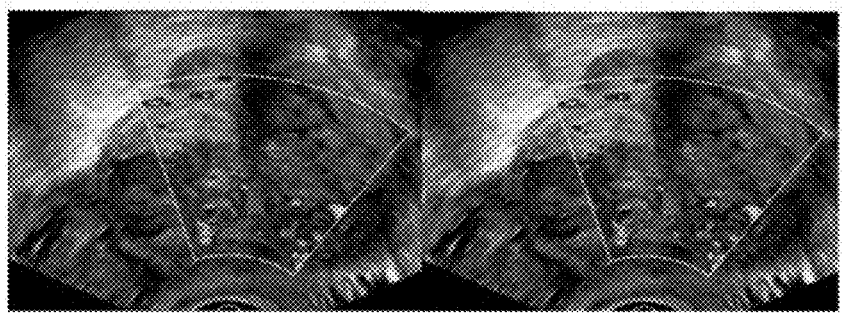

FIG. 5C: example of flash artefact removal. This video consists of 138 frames, recorded at 57 fps; the algorithm has set an acceptance threshold of 16 consecutive activation frames.

Figure 5D:
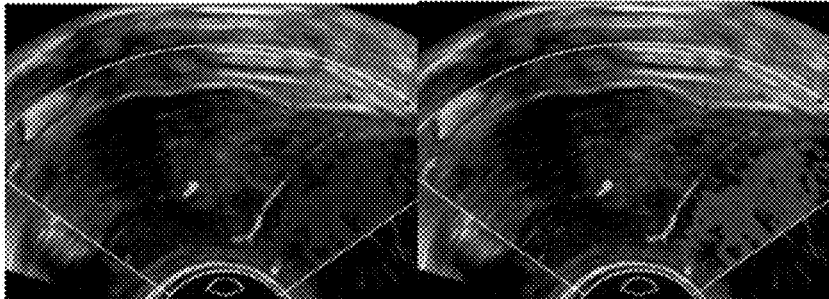

FIG. 5D: example of pseudoflow artefact removal. This video is composed of 499 frames, recorded with 57 fps; the algorithm has set an acceptance threshold of 19 consecutive activation frames.

Figure 5E:
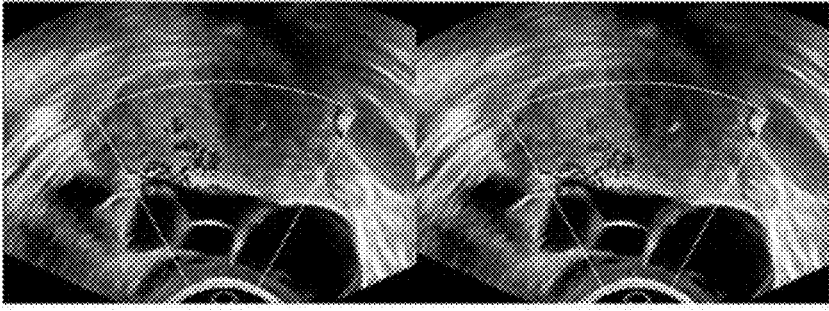

FIG. 5E: example of random and blooming artefact removal. This video consists of 229 frames, recorded at 57 fps; the algorithm has set an acceptance threshold of 14 consecutive activation frames.

According to the present embodiment, the n-frames with their corresponding pixels are overlapping and the relative j-th pixels in p×q position (height×width) are corresponding since each frame has the same dimensions and, e.g. on the basis of the machine performing the ultrasound video, the stationarity is high.

Figure 8:
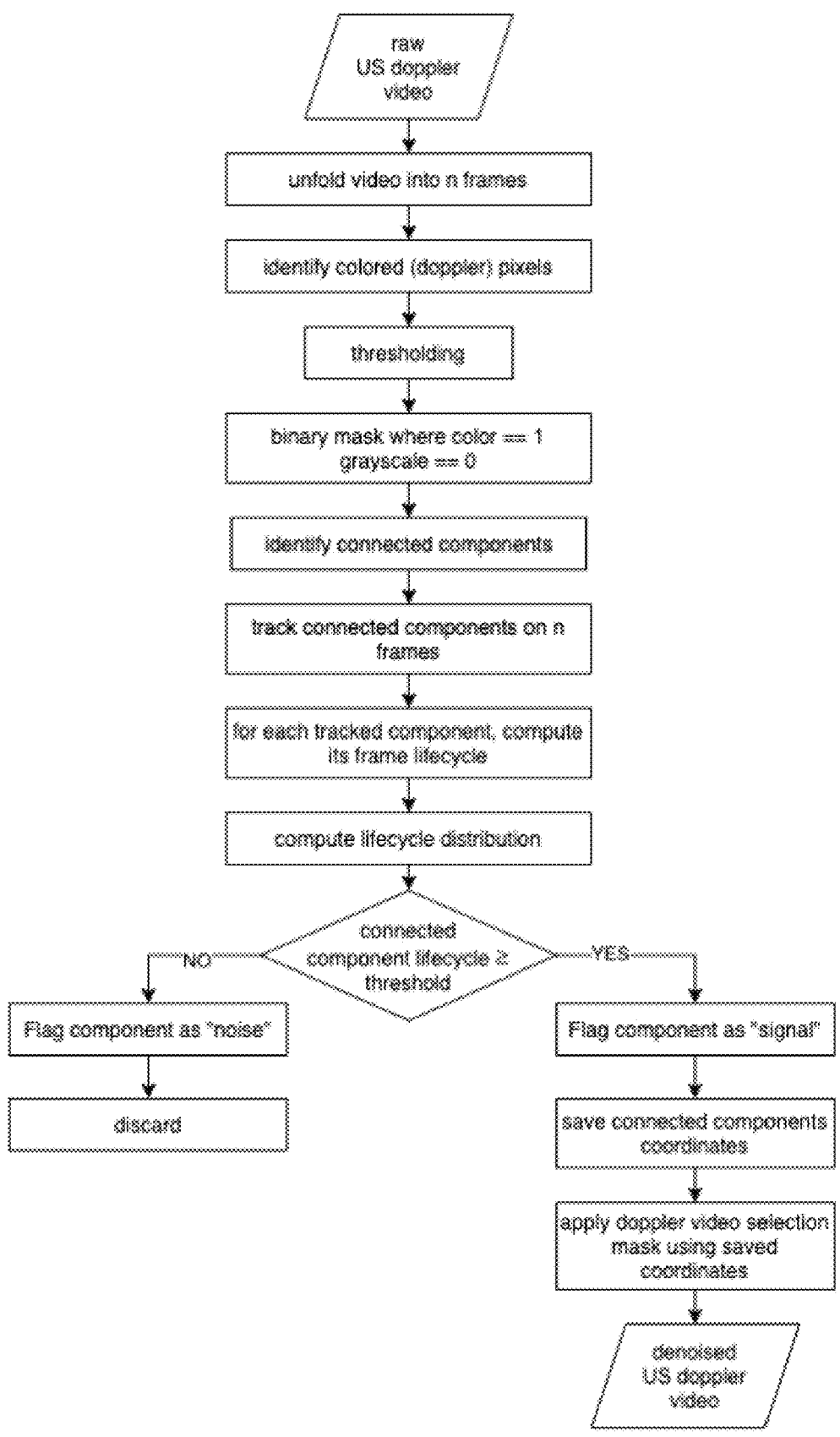
FIG. 8 shows a flow chart of the denoising process.

FIG. 8 shows the method of artefact removal flowchart of a doppler video in which are visible the steps sequence described above and that allow to obtain a video without artefacts or with a significant reduction of them.

What is claimed is:

1. A computer-implemented denoising method for removing artefacts from a doppler-type ultrasound video, comprising steps of:

acquiring a plurality (n) of frames composing an ultrasound video;

identifying for each of the n frames a first pixel category representative of first pixels of an n-th frame containing ultrasound signal; and a second pixel category representative of second pixels of an n-th frame containing doppler activation;

generating for each frame belonging to the plurality of frames, a first set of image data in order to associate to each pixel position of the corresponding frame at least a first or a second category so as to categorize the pixels of the corresponding frame and identifying for each frame the pixels containing doppler activation;

generating at least a persistence sequence associated to a frame portion containing identification data ordered according to a frame sequence such that adjacent identification data in the frame sequence refers to consecutive frames, wherein each identification data assumes a first value if the corresponding frame portion contains doppler activated pixels or a second value different from the first value if the corresponding frame portion does not contain doppler activated pixels;

in the persistence sequence associated with the frame portion, calculating a length of each persistence subsequence comprising consecutive identification data having the first value;

calculating a reference threshold based on length distribution of the persistence sub-sequences referring to whole identification data for the n frames;

identifying for each of the n frames a second set of image data (SEED) in order to associate to each pixel position in the corresponding frame:

wherein the information that the pixel position belongs to the second category when the frame n corresponds to one of the persistence sub-sequences having a length greater than the threshold so as to be representative of a pixel with real doppler signal; or the information that the pixel position belongs to the first category when the frame n corresponds to another one of the persistence sub-sequences having a length shorter than the threshold so as to be representative of an artefact; and removing from the corresponding frame a pixel at the pixel position identified as being representative of the artifact.

2. The computer-implemented denoising method according to claim 1, wherein the frame portion is a pixel of the frame and the step of generating comprises the step of generating a plurality of persistence sequences, one for each pixel of the plurality of frames format.

3. The computer-implemented denoising method according to claim 1, comprising the step of executing an algorithm for searching connected components comprising pixels of the first category on a frame n, and a frame n+1 to define the portions of the frame; wherein the step of generating the persistence sequence comprises the step of comparing a first parameter of a first connected component of frame n and a second parameter of a second connected component of frame n+1 and associating the second connected component with a first persistence sequence of the first connected component or generating a second persistence sequence of the second connected component on the basis of the step of comparing, in order to obtain a tracking of the connected components between the frame n and the frame n and frame n+1, the parameter being preferably a centroid and/or a parameter representative of overlapping of the first connected component and the second connected component and/or a parameter representing the similarity of shape of the first connected component and the second connected component and/or a parameter of size or dimension of the first connected component and the second connected component.

4. The computer-implemented denoising method according to claim 2, wherein the step of identifying the second image data set (SEED) is performed on the basis of a search algorithm for connected components to identify areas representative of the real doppler signal and comprising the steps of performing a segmentation algorithm based on a search for connected components of pixels of the second category on at least one n-th frame of the ultrasound video, comparing the connected components of the second category and connected components representative of the real doppler signal on the basis of an overlapping criteria, and deactivating the connected components of the second category which do not satisfy the overlapping criteria to obtain a region growing effect of the connected components representative of the real doppler signal.

5. The computer-implemented denoising method according to claim 1, wherein the step of identifying the second pixel category is performed according to a plurality of sub-categories, one for each doppler activation colour existing in the frame.

6. The computer-implemented denoising method according to claim 1, wherein the step of identifying the second category of pixels is performed by clustering.

7. The computer-implemented denoising method according to claim 1, wherein the step of identifying the second category of pixels is performed by selection via intensity difference of the R, G, B channels.

8. The computer-implemented denoising method according to claim 2, wherein a threshold calculation step is performed by calculation of the 90th percentile on distribution of lengths of the sub-sequences whose consecutive identifying data have a first representative doppler activation value or on the basis of the sum of the average with twice of a standard deviation of the lengths of the sub-sequences whose consecutive identification data have the first representative value of doppler activations.

9. The computer-implemented denoising method according to claim 3, wherein the step of calculating the threshold is performed by calculation of the 98th percentile on distribution of activation lengths or on the basis of the sum of the average with twice the standard deviation of the lengths of the sub-sequences whose consecutive identification data have the first representative value of doppler activations.

10. The computer-implemented denoising method according to claim 1, wherein the threshold calculation is performed by colour labelling for each pixel resulting from a previous step and the use of a classifier trained to extract the main colours found in an image.

11. The computer-implemented denosing method according to claim 1, wherein the denoised frames have values of the R, G, B channels equal to those of the original frame if represented coloured, and an average value if represented in grey scale.

12. The computer-implemented denoising method according to claim 4, wherein the region growing is performed by means of a method of morphological erosion and expansion with kernels of 5 pixels in diameter or side length and threshold value of 10%.

13. The computer-implemented denoising method according to claim 1, wherein the frame can be represented as a three-dimensional matrix.

14. The computer-implemented denoising method according to claim 1, further comprising the step of displaying the n-th frame, wherein the pixels corresponding to the real doppler signal are retained and the pixels corresponding to an artifact are modified.

15. The computer-implemented denoising method according to claim 2, further comprising the step of displaying the n-th frame, wherein the pixels corresponding to the real doppler signal are retained and the pixels corresponding to an artifact are modified.

16. The computer-implemented denoising method according to claim 3, further comprising the step of displaying the n-th frame, wherein the pixels corresponding to the real doppler signal are retained and the pixels corresponding to an artifact are modified.

17. The computer-implemented denoising method according to claim 4, further comprising the step of displaying the n-th frame, wherein the pixels corresponding to the real doppler signal are retained and the pixels corresponding to an artifact are modified.

18. The computer-implemented denoising method according to claim 5, further comprising the step of displaying the n-th frame, wherein the pixels corresponding to the real doppler signal are retained and the pixels corresponding to an artifact are modified.

19. The computer-implemented denoising method according to claim 6, further comprising the step of displaying the n-th frame, wherein the pixels corresponding to the real doppler signal are retained and the pixels corresponding to an artifact are modified.

20. The computer-implemented denoising method according to claim 7, further comprising the step of displaying the n-th frame, wherein the pixels corresponding to the real doppler signal are retained and the pixels corresponding to an artifact are modified.

\* \* \* \* \*